(12) United States Patent
Mants

(10) Patent No.: US 7,300,425 B1
(45) Date of Patent: Nov. 27, 2007

(54) CIRCULAR ABSORBENT ARTICLE WITH RAISED ABSORBENT BODY

(75) Inventor: Shanell Marie Mants, 15483 Patricia Dale Dr., Baton Rouge, LA (US) 70819

(73) Assignee: Shanell Marie Mants

( * ) Notice: Subject to any disclaimer, the term of this patent is extended or adjusted under 35 U.S.C. 154(b) by 0 days.

(21) Appl. No.: 11/633,898

(22) Filed: Dec. 5, 2006

(51) Int. Cl.
*A61F 13/15* (2006.01)
*A61F 13/20* (2006.01)

(52) U.S. Cl. .................. 604/385.01; 604/367; 604/370; 604/378

(58) Field of Classification Search ........... 604/385.01, 604/367, 370, 378, 385.07, 385.101, 385.03, 604/358; 450/37
See application file for complete search history.

(56) References Cited

U.S. PATENT DOCUMENTS 3,356,090 A * 12/1967 Plantinga et al. ........... 604/368
5,931,717 A * 8/1999 Lidji .......................... 450/37

* cited by examiner

*Primary Examiner*—Michele Kidwell

(57) ABSTRACT

A new and unique, multi-purpose sanitary napkin is designed and intended for wearers with an excessive flow of fluids. The sanitary napkin has a super absorbent core which gives maximum protection, against the wearer skin and garments, from extremely heavy menstrual cycles, post pregnancy and urinary incontinence.

5 Claims, 3 Drawing Sheets

Side View (Core Pad)

CIRCULAR ABSORBENT ARTICLE WITH RAISED ABSORBENT BODY

FIELD OF INVENTION

The present invention relates to an absorbent sanitary napkin to retain fluids of the wearer's skin and garments, pertaining to the flow of bodily fluids.

BACKGROUND OF INVENTION

The present invention relates to a unique, multi-purpose absorbent sanitary napkin, more particularly; to a sanitary napkin that is wider than that of a conventional sanitary napkin and is more absorbent, non-bulky, and flexible and will actually protect more. Most conventional sanitary napkins are narrow in width, which can cause fluid to flow down the inner thighs/legs, leaking onto the wearer garments. In the use of a conventional sanitary napkin, excessive fluid flow saturate, mostly, the middle of the napkin and flow outward, side to side, rather than up or down, which causes fluid to leak onto skin and garments, whether under or outer, or both. That is an inconvenience, and also an economic waste, when only two thirds of the product is being used. The conventional sanitary napkin is not flexible and does not provide maximum protection for the wearer. Especially, during the use of exercise, whether walking, running/jogging, stretching, bending or just switching positions from sitting or lying to standing or opening and closing of legs. The diameter of the wings is not wide enough to cover and protect, as a result, fluids can still flow pass the wings, onto the wearer's garments. Most conventional sanitary napkins does not absorb well enough to keep fluids from skin and flowing onto garments, therefore does not protect against orders well. Lastly, as the body temperature of the wearer increases and perspiration begins, the adhesive beings to weaken and cause the sanitary napkin to shift around, leaving the wearer uncomfortable and insecure. The conventional sanitary napkin is simply not designed to meet the need of every wearer, which is of different shapes and sizes.

SUMMARY OF INVENTION

The invention of the unique absorbent sanitary napkin is to resolve the above mentioned drawbacks and to provide a dependable, multi-purpose absorbent sanitary napkin for wearers with any level flow of bodily fluids. The 360 degree circular shape is to provide a wider range of protection against the wearer's skin and clothing. The probability of the improved sanitary napkin becoming more saturated than the conventional sanitary napkin is greater because the shape allows accommodate the flow of fluids, in a circular shape. The sanitary napkin is more convenient because of its flexibility. The sanitary napkin is designed to move as you move giving the wearer the maximum protection even while walking, running/jogging, stretching, bending or just switching positions from sitting or lying to standing and opening and closing of legs. The wing, per-se, is designed to lie next to the skin in the inner thigh to prevent fluids from leaking onto garments. The sanitary napkin is designed to meet the needs of wearers of different shapes and sizes. The sanitary napkin is guaranteed to give more protection, day or night, than that of a conventional sanitary napkin.

BRIEF DESCRIPTION OF THE DRAWINGS

The invention will be better understood by reference to the accompanying drawings, in which.

DESCRIPTION OF THE PREFERRED EMBODIMENTS

An embodiment of the present invention will be described by referring to the accompanying drawings.

Figure 1:
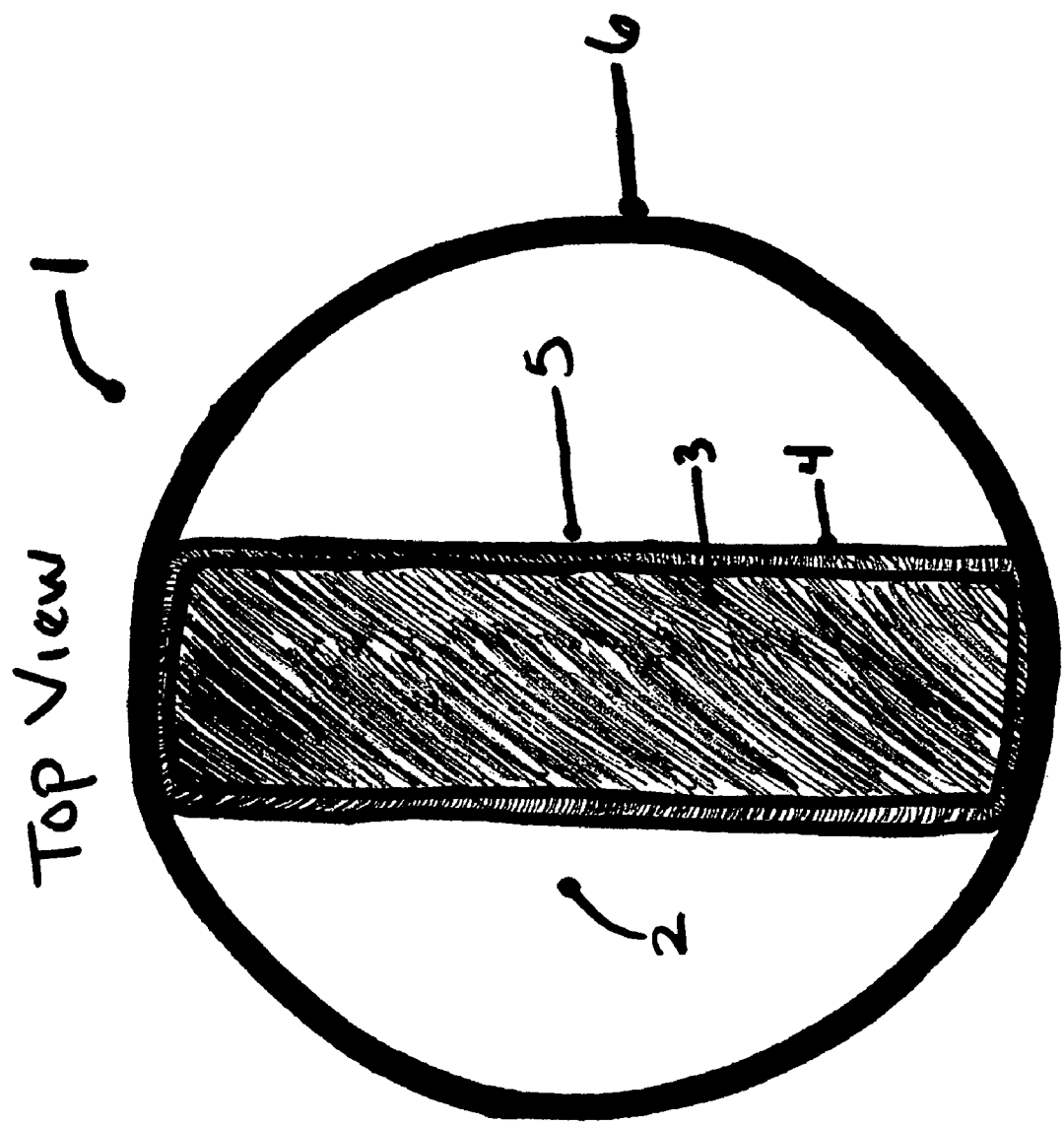
FIG. 1 is a perspective view of the circular shaped absorbent sanitary napkin of the present invention.
Figure 2:
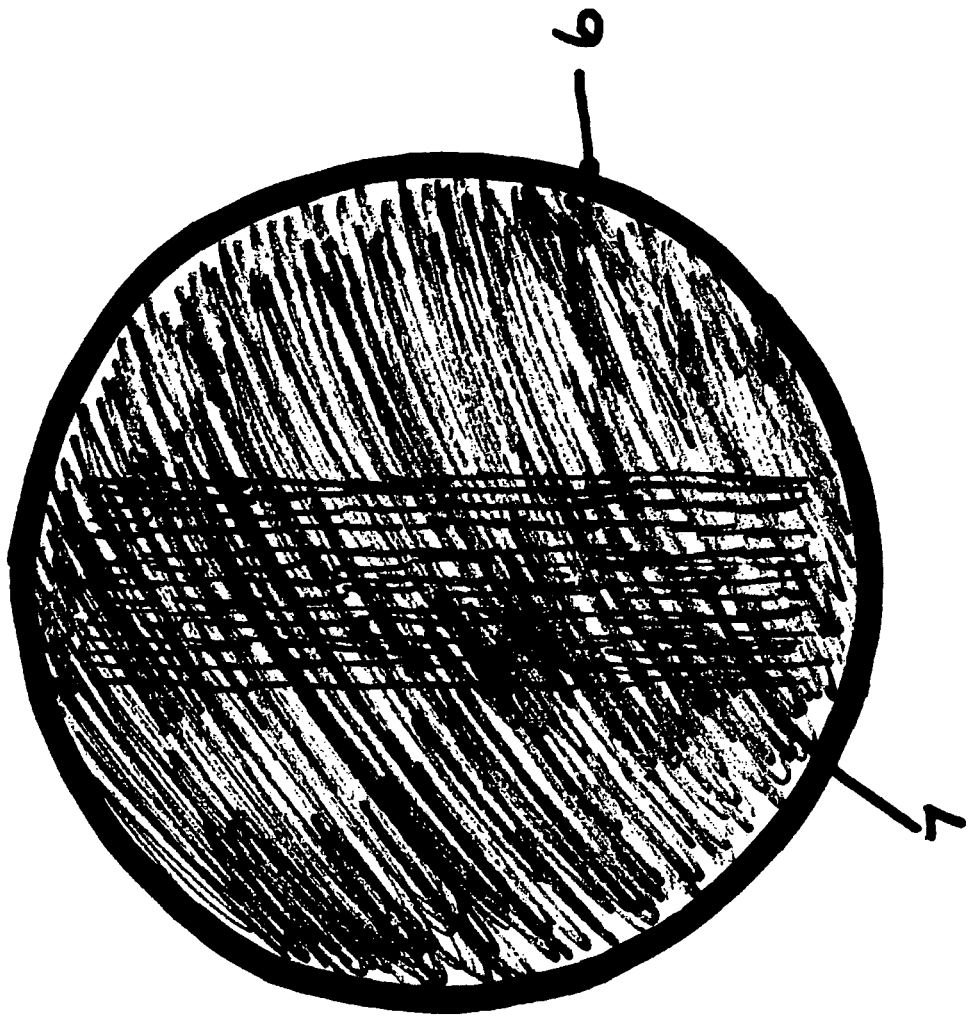
FIG. 2 is a bottom view of the circular shaped absorbent sanitary napkin.

FIG. 1 is a plain top view of the absorbent sanitary napkin with numbers referring to the layers of the present invention;

FIG. 2 is the bottom view thereof.

Figure 3:
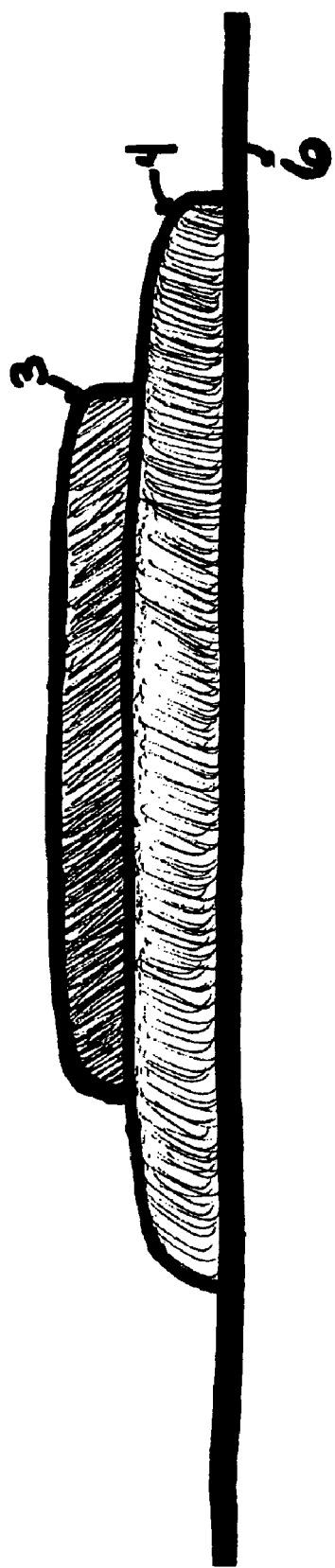
FIG. 3 is a side view of the interposed core pad.

FIG. 3 is the core pad interposed between the top and bottom sheets.

The present invention is generally indicated by reference numeral 1. An absorbent sanitary napkin 1 is worn by the wearer to absorb and retain bodily fluids away from the skin and clothing of wearer. The absorbent sanitary napkin consists of multi layers, of any absorbent materials, which allow the present invention to be more efficient and effective.

The absorbent sanitary napkin includes a first and second body group. The first body group consists of reference numbers 2, 5, 6, 7. The second body group consists of reference numbers 3 and 4 which is interposed between the super absorbent polymer 5 and the flame retardant non woven facing 2.

This absorbent sanitary napkin 1 has a flame retardant non-woven facing 2, which allow more air flow and better absorbency. The joined, center napkin body 3, is an elongated configuration, as shown, with a curved front end and curved rear end. This absorbent, center napkin body is made up of an upper layer, one or more middle layers; the center napkin core 4, which is usually consisted of cotton and a liquid impervious bottom layer.

Joined to layer 4, is the super-absorbent polymer 5, which provides additional protection that the center napkin may not absorb.

This layer is excellent against fluid retention, improves dryness and reduces odor. The bottom layer is a waterproof embossed blue polypropylene backing 6, which may also be substituted with polyethylene. This backing folds ½ inch over onto the non-woven facing 2, to seal and lock in fluids to prevent leakage and retract fluids off the wearer skin and clothing.

The present invention of the absorbent sanitary napkin is designed for the center napkin body 3, to contour the crotch of the wearer, while the extended flaps, the wings, per-se, lay against the inner thighs of the wearer to retract fluids away from skin and clothing.

Let it be known that the foregoing description of the absorbent sanitary napkin 1 may have characteristics and features which depart from those previously described of the present invention. For example, a medicated gel, (not shown) used to prevent irritation of the wearer skin. Another example would be an adhesive strip 7, provided on the back of the bottom layer, blue polypropylene backing 6, alone or in combination with the "wings" per-se, to secure attachment of the absorbent sanitary napkin 1, to the undergarment of the wearer.

Let it be known that the present invention of the absorbent sanitary napkin may be of any size, any color and different shapes.

While the preferred embodiments of the invention have been described above, it will be recognized and understood that various modifications can be made to the invention and the appended claims are intended to cover all such modifications which may fall within the same line of the invention.

Having described my invention, I hereby claim:

1. A circular-shaped sanitary napkin, comprising a first body group and a second body group, wherein the first body group consists of:
   a) a liquid-pervious, flame-retardant nonwoven facing,
   b) a superabsorbent polymer layer,
   c) a waterproof, embossed, blue, polypropylene backing joined to and folding ½ inch over onto the nonwoven facing, and
   d) an adhesive strip provided on the bottom of the backing;
   wherein the second body group consists of:
   a) a center napkin body, and
   b) a raised center napkin core;
   such that the second body group, in addition to the superabsorbent polymer layer of the first body group, completely extend along a longitudinal centerline of the sanitary napkin and is limited to the center of the sanitary napkin with respect to the diameter of the sanitary napkin;
   wherein the second body group is interposed between the superabsorbent polymer and the liquid-pervious, flame-retardant nonwoven facing of the first body group.

2. The sanitary napkin according to claim 1, wherein said sanitary napkin comprises an elongated configuration.

3. The sanitary napkin according to claim 1, wherein said raised center napkin core comprises cotton.

4. The sanitary napkin according to claim 1, wherein said sanitary napkin comprises one or more liquid absorbent layer(s) and one or more liquid impervious layer(s).

5. The sanitary napkin according to claim 1, wherein the sanitary napkin is disposable.

* * * * *